United States Patent [19]

Nelson

[11] 4,110,382

[45] Aug. 29, 1978

[54] 2-DECARBOXY-2-HYDROXY-METHYL-ω-PHENYL-PGE ANALOGS

[75] Inventor: Norman A. Nelson, Galesburg, Mich.

[73] Assignee: The Upjohn Company, Kalamazoo, Mich.

[21] Appl. No.: 822,035

[22] Filed: Aug. 5, 1977

Related U.S. Application Data

[62] Division of Ser. No. 647,357, Jan. 8, 1976, Pat. No. 4,055,602.

[51] Int. Cl.$^2$ ............................................. C07C 49/82
[52] U.S. Cl. ................................................ 260/590 C
[58] Field of Search ..................... 250/590 C; 560/121

*Primary Examiner*—James O. Thomas, Jr.

*Assistant Examiner*—James H. Reamer
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

119 Claims, No Drawings

2-DECARBOXY-2-HYDROXY-METHYL-ω-PHENYL-PGE ANALOGS

The present application is a divisional application of Ser. No. 647,357, filed Jan. 8, 1976, now issued as U.S. Pat. No. 4,055,602.

The present invention relates to prostaglandin analogs, for which the essential material constituting disclosure therefor is incorporated by reference here from U.S. Pat. No. 4,055,602, issued Oct. 25, 1977.

I claim:

1. A prostaglandin analog of the formula

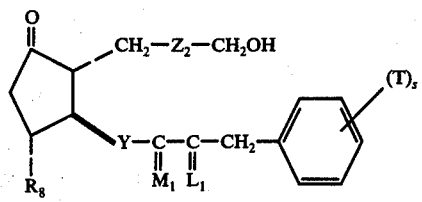

wherein $R_8$ is hydrogen or hydroxy;
wherein Y is trans-CH=CH—;
wherein $M_1$ is

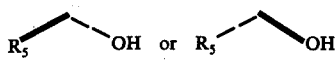

wherein $R_5$ is hydrogen or methyl;
wherein $L_1$ is

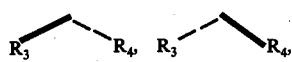

or a mixture of

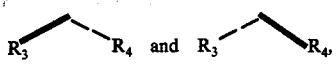

wherein $R_3$ and $R_4$ are hydrogen, methyl, or fluoro, being the same or different, with the proviso that one of $R_3$ and $R_4$ is methyl only when the other is hydrogen or methyl;
wherein $Z_2$ is
cis-CH=CH—CH$_2$—(CH$_2$)$_g$—CF$_2$—;
cis-CH$_2$—CH=CH—(CH$_2$)$_g$—CH$_2$—; or
—(CH$_2$)$_3$—(CH$_2$)$_g$—CF$_2$—;
wherein $g$ is one, 2, or 3; and
wherein $s$ is zero, one, 2, or 3 and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl.

2. A compound according to claim 1, wherein $R_8$ is hydrogen.

3. A compound according to claim 2, wherein $s$ is zero or one and T is chloro, fluoro, or trifluoromethyl.

4. A compound according to claim 3, wherein $Z_2$ is cis-CH=CH—CH$_2$—(CH$_2$)$_g$—CF$_2$—.

5. A compound according to claim 4, wherein $g$ is one.

6. A compound according to claim 5, wherein at least one of $R_3$ and $R_4$ is fluoro.

7. A compound according to claim 6, wherein $R_3$ and $R_4$ are both fluoro.

8. A compound according to claim 7, wherein $R_5$ is methyl.

9. 2-Decarboxy-2-hydroxymethyl-2,2,16,16-tetrafluoro-15-methyl-17-phenyl-18,19,20-trinor-11-deoxy-PGE$_2$, a compound according to claim 8.

10. A compound according to claim 7, wherein $R_5$ is hydrogen.

11. 2-Decarboxy-2-hydroxymethyl-2,2,16,16-tetrafluoro-17-phenyl-18,19,20-trinor-11-deoxy-PGE$_2$, a compound according to claim 10.

12. A compound according to claim 5, wherein at least one of $R_3$ and $R_4$ is methyl.

13. A compound according to claim 12, wherein $R_3$ and $R_4$ are both methyl.

14. A compound according to claim 13, wherein $R_5$ is methyl.

15. 2-Decarboxy-2-hydroxymethyl-2,2-difluoro-15,16,16-trimethyl-17-phenyl-18,19,20-trinor-11-deoxy-PGE$_2$, a compound according to claim 14.

16. A compound according to claim 13, wherein $R_5$ is hydrogen.

17. 2-Decarboxy-2-hydroxymethyl-2,2-difluoro-16,16-dimethyl-17-phenyl-18,19,20-trinor-11-deoxy-PGE$_2$, a compound according to claim 16.

18. A compound according to claim 5, wherein $R_3$ and $R_4$ are both hydrogen.

19. A compound according to claim 18, wherein $R_5$ is hydrogen.

20. 2-Decarboxy-2-hydroxymethyl-2,2-difluoro-15-methyl-17-phenyl-18,19,20-trinor-11-deoxy-PGE$_2$, a compound according to claim 19.

21. A compound according to claim 18, wherein $R_5$ is hydrogen.

22. 2-Decarboxy-2-hydroxymethyl-2,2-difluoro-17-phenyl-18,19,20-trinor-11-deoxy-PGE$_2$, a compound according to claim 21.

23. A compound according to claim 3, wherein $Z_2$ is —(CH$_2$)$_3$—(CH$_2$)$_g$—CF$_2$—.

24. A compound according to claim 23, wherein $g$ is one.

25. A compound according to claim 24, wherein at least one of $R_3$ and $R_4$ is fluoro.

26. A compound according to claim 25, wherein $R_3$ and $R_4$ are both fluoro.

27. A compound according to claim 26, wherein $R_5$ is methyl.

28. 2-Decarboxy-2-hydroxymethyl-2,2,16,16-tetrafluoro-15-methyl-17-phenyl-18,19,20-trinor-11-deoxy-PGE$_1$, a compound according to claim 27.

29. A compound according to claim 26, wherein $R_5$ is hydrogen.

30. 2-Decarboxy-2-hydroxymethyl-2,2,16,16-tetrafluoro-17-phenyl-18,19,20-trinor-11-deoxy-PGE$_1$, a compound according to claim 29.

31. A compound according to claim 24, wherein at least one of $R_3$ and $R_4$ is methyl.

32. A compound according to claim 31, wherein $R_3$ and $R_4$ are both methyl.

33. A compound according to claim 32, wherein $R_5$ is methyl.

34. 2-Decarboxy-2-hydroxymethyl-2,2-difluoro-15,16,16-trimethyl-17-phenyl-18,19,20-trinor-11-deoxy-PGE$_1$, a compound according to claim 33.

35. A compound according to claim 32, wherein $R_5$ is hydrogen.

36. 2-Decarboxy-2-hydroxymethyl-2,2-difluoro-16,16-dimethyl-17-phenyl-18,19,20-trinor-11-deoxy-PGE$_1$, a compound according to claim 35.

37. A compound according to claim 24, wherein R$_3$ and R$_4$ are both hydrogen.

38. A compound according to claim 37, wherein R$_5$ is methyl.

39. 2-Decarboxy-2-hydroxymethyl-2,2-difluoro-15-methyl-17-phenyl-18,19,20-trinor-11-deoxy-PGE$_1$, a compound according to claim 38.

40. A compound according to claim 37, wherein R$_5$ is hydrogen.

41. 2-Decarboxy-2-hydroxymethyl-2,2-difluoro-17-phenyl-18,19,20-trinor-11-deoxy-PGE$_1$, a compound according to claim 40.

42. A compound according to claim 3, wherein Z$_2$ is cis-CH$_2$—CH=CH—(CH$_2$)$_g$—CH$_2$—.

43. A compound according to claim 42, wherein $g$ is one.

44. A compound according to claim 43, wherein at least one of R$_3$ and R$_4$ is fluoro.

45. A compound according to claim 44, wherein R$_3$ and R$_4$ are both fluoro.

46. A compound according to claim 45, wherein R$_5$ is methyl.

47. 2-Decarboxy-2-hydroxymethyl-cis-4,5-didehydro-15-methyl-16,16-difluoro-17-phenyl-18,19,20-trinor-11-deoxy-PGE$_1$, a compound according to claim 46.

48. A compound according to claim 45, wherein R$_5$ is hydrogen.

49. 2-Decarboxy-2-hydroxymethyl-cis-4,5-didehydro-16,16-difluoro-17-phenyl-18,19,20-trinor-11-deoxy-PGE$_1$, a compound according to claim 48.

50. A compound according to claim 43, wherein at least one of R$_3$ and R$_4$ is methyl.

51. A compound according to claim 50, wherein R$_3$ and R$_4$ are both methyl.

52. A compound according to claim 51, wherein R$_5$ is methyl.

53. 2-Decarboxy-2-hydroxymethyl-cis-4,5-didehydro-15,16,16-trimethyl-17-phenyl-18,19,20-trinor-11-deoxy-PGE$_1$, a compound according to claim 52.

54. A compound according to claim 51, wherein R$_5$ is hydrogen.

55. 2-Decarboxy-2-hydroxymethyl-cis-4,5-didehydro-16,16-dimethyl-17-phenyl-18,19,20-trinor-11-deoxy-PGE$_1$, a compound according to claim 54.

56. A compound according to claim 43, wherein R$_3$ and R$_4$ are both hydrogen.

57. A compound according to claim 56, wherein R$_5$ is methyl.

58. 2-Decarboxy-2-hydroxymethyl-cis-4,5-didehydro-15-methyl-17phenyl-18,19,20-trinor-11-deoxy-PGE$_1$, a compound according to claim 57.

59. A compound according to claim 56, wherein R$_5$ is hydrogen.

60. 2-Decarboxy-2-hydroxymethyl-cis-4,5-didehydro-17-phenyl-18,19,20-trinor-11-deoxy-PGE$_1$, a compound according to claim 59.

61. A compound according to claim 1, wherein R$_8$ is hydroxy.

62. A compound according to claim 61, wherein $s$ is zero or one and T is chloro, fluoro, or trifluoromethyl.

63. A compound according to claim 62, wherein Z$_2$ is cis-CH=CH—CH$_2$—(CH$_2$)$_g$—CF$_2$—.

64. A compound according to claim 63, wherein $g$ is one.

65. A compound according to claim 64, wherein at least one of R$_3$ and R$_4$ is fluoro.

66. A compound according to claim 65, wherein R$_3$ and R$_4$ are both fluoro.

67. A compound according to claim 66, wherein R$_5$ is methyl.

68. 2-Decarboxy-2-hydroxymethyl-2,2,16,16-tetrafluoro-15-methyl-17-phenyl-18,19,20-trinor-PGE$_2$, a compound according to claim 67.

69. A compound according to claim 66, wherein R$_5$ is hydrogen.

70. 2-Decarboxy-2-hydroxymethyl-2,2,16,16-tetrafluoro-17-phenyl-18,19,20-trinor-PGE$_2$, a compound according to claim 69.

71. A compound according to claim 64, wherein at least one of R$_3$ and R$_4$ is methyl.

72. A compound according to claim 71, wherein R$_3$ and R$_4$ are both methyl.

73. A compound according to claim 72, wherein R$_5$ is methyl.

74. 2-Decarboxy-2-hydroxymethyl-2,2-difluoro-15,16,16-trimethyl-17-phenyl-18,19,20-trinor-PGE$_2$, a compound according to claim 73.

75. A compound according to claim 72, wherein R$_5$ is hydrogen.

76. 2-Decarboxy-2-hydroxymethyl-2,2-difluoro-16,16-dimethyl-17-phenyl-18,19,20-trinor-PGE$_2$, a compound according to claim 75.

77. A compound according to claim 64, wherein R$_3$ and R$_4$ are both hydrogen.

78. A compound according to claim 77, wherein R$_5$ is hydrogen.

79. 2-Decarboxy-2-hydroxymethyl-2,2-difluoro-15-methyl-17-phenyl-18,19,20-trinor-PGE$_2$, a compound according to claim 78.

80. A compound according to claim 77, wherein R$_5$ is hydrogen.

81. 2-Decarboxy-2-hydroxymethyl-2,2-difluoro-17-phenyl-18,19,20-trinor-PGE$_2$, a compound according to claim 80.

82. A compound according to claim 62, wherein Z$_2$ is —(CH$_2$)$_3$—(CH$_2$)$_g$—CF$_2$—.

83. A compound according to claim 82, wherein $g$ is one.

84. A compound according to claim 83, wherein at least one of R$_3$ and R$_4$ is fluoro.

85. A comound according to claim 84, wherein R$_3$ and R$_4$ are both fluoro.

86. A compound according to claim 85, wherein R$_5$ is methyl.

87. 2-Decarboxy-2-hydroxymethyl-2,2,16,16-tetrafluoro-15-methyl-17-phenyl-18,19,20-trinor-PGE$_1$, a compound according to claim 86.

88. A compound according to claim 85, wherein R$_5$ is hydrogen.

89. 2-Decarboxy-2-hydroxymethyl-2,2,16,16-tetrafluoro-17-phenyl-18,19,20-trinor-PGE$_1$, a compound according to claim 88.

90. A compound according to claim 83, wherein at least one of R$_3$ and R$_4$ is methyl.

91. A compound according to claim 90, wherein R$_3$ and R$_4$ are both methyl.

92. A compound according to claim 91, wherein R$_5$ is methyl.

93. 2-Decarboxy-2-hydroxymethyl-2,2-difluoro-15,16,16-trimethyl-17-phenyl-18,19,20-trinor-PGE$_1$, a compound according to claim 92.

94. A compound according to claim 91, wherein $R_5$ is hydrogen.

95. 2-Decarboxy-2-hydroxymethyl-2,2-difluoro-16,16-dimethyl-17-phenyl-18,19,20-trinor-$PGE_1$, a compound according to claim 94.

96. A compound according to claim 83, wherein $R_3$ and $R_4$ are both hydrogen.

97. A compound according to claim 96, wherein $R_5$ is methyl.

98. 2-Decarboxy-2-hydroxymethyl-2,2-difluoro-15-methyl-17-phenyl-18,19,20-trinor-$PGE_1$, a compound according to claim 97.

99. A compound according to claim 96, wherein $R_5$ is hydrogen.

100. 2-Decarboxy-2-hydroxymethyl-2,2-difluoro-17-phenyl-18,19,20-trinor-$PGE_1$, a compound according to claim 99.

101. A compound according to claim 62, wherein $Z_2$ is cis-$CH_2$—$CH$=$CH$—$(CH_2)_g$—$CH_2$—.

102. A compound according to claim 101, wherein $g$ is one.

103. A compound according to claim 102, wherein at least one of $R_3$ and $R_4$ is fluoro.

104. A compound according to claim 103, wherein $R_3$ and $R_4$ are both fluoro.

105. A compound according to claim 104, wherein $R_5$ is methyl.

106. 2-Decarboxy-2-hydroxymethyl-cis-4,5-didehydro-15-methyl-16,16-difluoro-17-phenyl-18,19,20-trinor-$PGE_1$, a compound according to claim 105.

107. A compound according to claim 104, wherein $R_5$ is hydrogen.

108. 2-Decarboxy-2-hydroxymethyl-cis-4,5-didehydro-16,16-difluoro-17-phenyl-18,19,20-trinor-$PGE_1$, a compound according to claim 107.

109. A compound according to claim 102, wherein at least one of $R_3$ and $R_4$ is methyl.

110. A compound according to claim 109, wherein $R_3$ and $R_4$ are both methyl.

111. A compound according to claim 110, wherein $R_5$ is methyl.

112. 2-Decarboxy-2-hydroxymethyl-cis-4,5-didehydro-15,16,16-trimethyl-17-phenyl-18,19,20-trinor-$PGE_1$ a compound according to claim 111.

113. A compound according to claim 110, wherein $R_5$ is hydrogen.

114. 2-Decarboxy-2-hydroxymethyl-cis-4,5-didehydro-16,16-dimethyl-17-phenyl-18,19,20-trinor-$PGE_1$, a compound according to claim 113.

115. A compound according to claim 102, wherein $R_3$ and $R_4$ are both hydrogen.

116. A compound according to claim 115, wherein $R_5$ is methyl.

117. 2-Decarboxy-2-hydroxymethyl-cis-4,5-didehydro-15-methyl-17-phenyl-18,19,20-trinor-$PGE_1$, a compound according to claim 116.

118. A compound according to claim 115, wherein $R_5$ is hydrogen.

119. 2-Decarboxy-2-hydroxymethyl-cis-4,5-didehydro-17-phenyl-18,19,20-trinor-$PGE_1$, a compound according to claim 118.

* * * * *